United States Patent [19]

Matsumura

[11] Patent Number: 5,050,612
[45] Date of Patent: Sep. 24, 1991

[54] DEVICE FOR COMPUTER-ASSISTED MONITORING OF THE BODY

[76] Inventor: Kenneth N. Matsumura, 2107 Dwight Way, Berkeley, Calif. 94704

[21] Appl. No.: 406,148

[22] Filed: Sep. 12, 1989

[51] Int. Cl.⁵ .............................................. A61B 5/02
[52] U.S. Cl. .................................. 128/670; 128/696; 128/710; 128/736; 604/55
[58] Field of Search ............... 128/670, 724, 736, 696, 128/710, DIG. 12, DIG. 13; 604/891.1, 55

[56] References Cited

U.S. PATENT DOCUMENTS

| | | | |
|---|---|---|---|
| 4,151,831 | 5/1979 | Lester | 128/736 |
| 4,270,547 | 6/1981 | Steffen | 128/736 |
| 4,297,685 | 10/1981 | Brainard | 128/736 |
| 4,387,724 | 6/1983 | Zartman | 128/736 |
| 4,619,653 | 10/1986 | Fischell | 128/DIG. 13 |
| 4,753,244 | 6/1988 | Landymore et al. | 128/696 |
| 4,874,359 | 10/1989 | White et al. | 128/DIG. 13 |

*Primary Examiner*—Francis Jaworski
*Assistant Examiner*—George Manuel

[57] ABSTRACT

A device for computer-assisted monitoring of body temperature and for detection of ovulation, for detection and treatment of life-threatening cardiac ischemia and arrythmia, and for detection and correction of abnormal elevation of glucose.

5 Claims, 12 Drawing Sheets

OMINOUS SIGNS BEFORE A HEART ATTACK

DEVICE FOR COMPUTER-ASSISTED MONITORING OF THE BODY

This invention is in the field of monitoring bodily functions and more specifically deals with continual measurements of body temperature, cardiac ischemia status, and blood sugar.

BACKGROUND OF THE INVENTION

It is useful to continually monitor certain bodily functions. For example, by monitoring basal body temperature over a period of weeks, one can determine the time of ovulation or detect the onset of viral illnesses such as the common cold early enough for certain anti-viral medications (e.g., amantadine) to thwart the progress of the disease. By monitoring the electrical activity of the heart, one can detect the onset of serious myocardial ischemia before it progresses to a heart attack (myocardial infarction). By continually monitoring the glucose levels to blood in diabetics, one can feed the data to a microprocessor that can control the infusion of insulin by a pump in correlation with the measured glucose level. For over a decade now, I have been working on and perfecting a device which I call CAMBY (TM), an acronym for Computer Assisted Monitoring of the Body, which is capable of the useful functions I have just delineated. This application describes each function of the device in detail.

Until the present invention, there has not been any device capable of reliably and continuously monitoring ovulation, cardiac ischemia, or elevated glucose levels. Typically, the basal body temperature is determined by taking one's temperature upon awakening. There are kits that allow one to measure the core body temperature upon arising in the morning by measuring the temperature of the first morning urine specimen. However, the temperature one measures upon awakening is not the basal body temperature (as explained below) and this method of guessing the basal body temperature is tedious and subject to many errors. There are portable monitors for monitoring electrocardiac activity of a subject and some of them are able to detect cardiac arrythmias, even providing for the automatic injection of anti-arrythmic medications. Currently marketed monitors are for very special use by only a limited number of people. However, there is no monitor suitable for more general use that detects and warns of the kind of cardiac ischemia that can lead imminently to a heart attack.

There are glucose-sensors which use enzyme-based systems for monitoring blood glucose, but despite over two decades of research no one has been able to develop a sensor that works reliably over a period of many weeks.

OBJECTS OF THE INVENTION

I have developed a device that is capable of continually monitoring the body temperature determining the basal body temperature accurately, monitoring the menstrual cycle and the time of ovulation, which is also capable of detecting and warning of an impending heart attack, administering appropriate medications to the monitored subject, and which is further capable of detecting and correcting an elevation in blood glucose. It is an objective of the invention that, at least in one embodiment, most of the functions of the device are centralized in a simple, user-friendly, economical wrist-mountable unit. Other objects and advantages of my invention will become evident in the description that follows.

HOW THIS SPECIFICATION IS ORGANIZED

All the functions of my invention use a central microprocessor fed by data from different sensing devices and use other sharable means such as analog to digital converter and voltage averager. Although my invention is an integrated, single device with multiple functions sharing one microcomputer, for sake of clarity, I have chosen to describe the device in its three separate functions as if each function constituted a separate device. Indeed, each function can be made up into a separate device, but because it could be helpful in many subjects that they receive the benefit of all these functions (e.g., a diabetic who needs to avoid pregnancy and who is subject to an early heart attack because of the chronic effect of diabetes), this application describes the multifunctional apparatus.

MONITORING OF BASAL BODY TEMPERATURE

Figure 1:
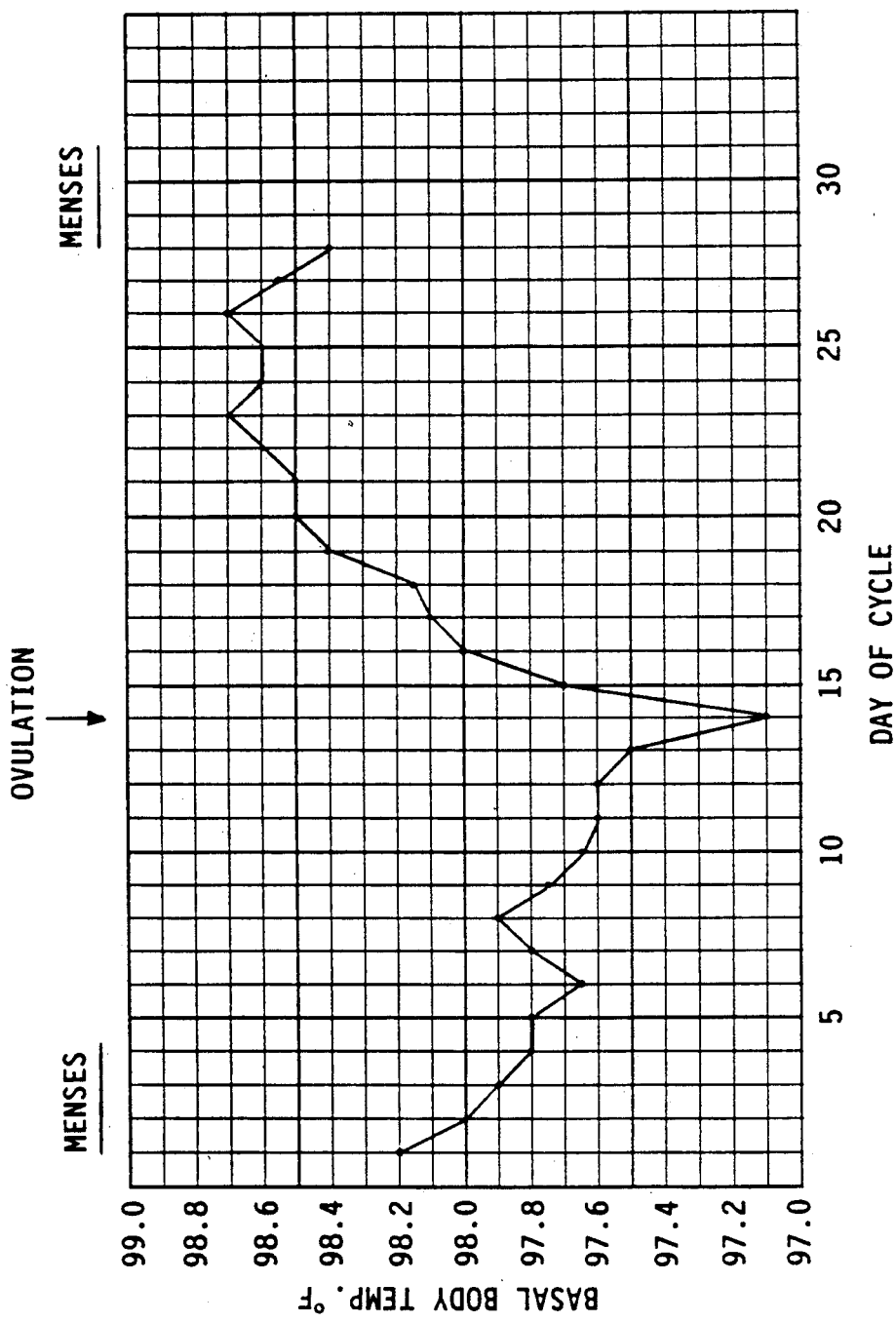
FIG. 1 is a chart of a typical basal body temperature of a subject over a course of one menstrual cycle, showing a characteristic dip and a rise at the time of ovulation.

This portion of the device does not merely measure body temperature. The uniqueness lies in the fact that the device is "smart." The invention measures body temperature continually while a subject is at rest at night and determines the subject's basal body temperature (the core temperature of the body most at rest in the diurnal cycle). The invention monitors the daily basal body temperature (BBT) over many weeks and determines the time of ovulation from the cylic changes in BBT reflecting the various menstrual phases of the subject (FIG. 1).

Figure 2:
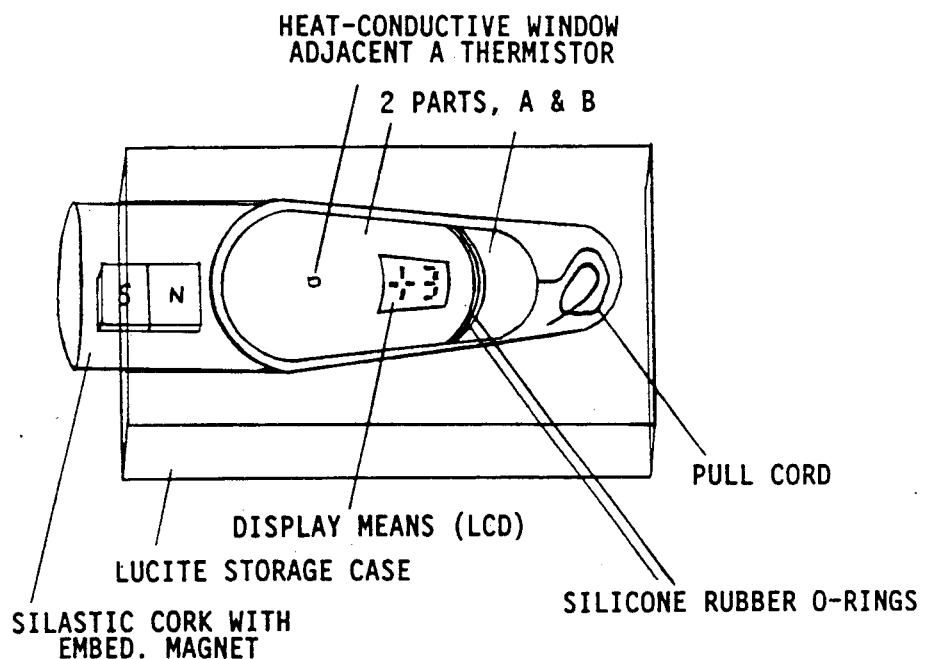
FIG. 2 is a perspective view of a basal body temperature monitor for vaginal use, shown in its water-tight carrier between use.

BBT DEVICE, TYPE 1. One embodiment of the invention monitors temperature in the vagina. The first device (FIG. 2) comprises: temperature sensing means; an analog to digital converter connected to said sensing means to convert the analog signal from said sensing means to digital signal; a microprocessor means connected to said converter to record and microprocess data from said sensing means; insulating material surrounding a temperature sensor apparatus of said sensing means so as to insulate said sensor from heat generated from said microprocessor; a small battery powering said sensing means, said converter, and said microprocessor; a switch intermittently turning on and off certain power drawing circuits; an externally controllable switch to enable switching on and off certain power drawing circuits from the outside of the device; all said means and recited components held and hermetically sealed inside a durable, light-weight, bio-compatible rotund housing; means to promote retention of the device within the vagina; means to facilitate intra-vaginal insertion and removal.

In a preferred embodiment, the device also comprises display means on an exterior aspect of said housing that is connected and fed by said microprocessor, said display means providing a read-out of valuable information calculated by the device which alerts the user on any given day whether the day is a "safe" (infertile) or a fertile one.

In another preferred embodiment, the device also comprises means for easily opening and hermetically-closing said housing to enable changing said battery or to provide access for other purposes to internal circuits. Such means may be provided by male and female threading of adjoining parts so that the two parts come together by being screwed together. The parts may be so arranged that when they come together, an electrical contact is achieved between the two parts to activate the electrical circuits. The display can be programmed to then read "ON" or "OK." Silicone rubber gasketting at the joint can be employed to provide for hermetic sealing of the housing.

More specifically, the temperature sensing means may be an electrical circuit containing a temperature sensing apparatus like the thermistor which causes a change in the electrical resistance in the circuit according to the change in temperature sensed by the thermistor. The change in resistance causes a change in electrical flow that can be measured. This analog measurement can be converted by an analog to digital converter into a digital signal which can be fed to a microprocessor for storage and interpretation. The thermistor preferably would be close to the exterior of said housing holding the components of the device, preferably adjacent to a good heat-conducting material. A thin 1 mm stainless steel plate would make a good material to which to be adjacent. Other metals that would not react poorly to vaginal acids would be also suitable. Actually, 1 mm thick plastic membrane, similar to the material used for said housing (e.g. polypropylene), should work under most conditions. The battery preferably would be a long-acting type, such as those of lithium. The means for intermittent switching is readily available from electronic parts suppliers. One type is available from Biotelemetrics, Inc. of Westlake, Ohio (SWP-1). The entire unit can be shut-off intermittently except those circuits used to hold stored information in the microprocessor. The microprocessor itself may double as an intermittent switch. Monitoring of the temperature need only be as infrequently as every 5 to 1 minutes. The means for switching the device off from the outside may be a magnet-sensitive switch, also readily available commercially. Such a switch breaks the circuit when the switch is in close proximity to a magnet.

Since the device is to be inserted and held inside the vagina, the housing should not have rough edges but should generally be rotund so as not to poke uncomfortably. Since the vagina, at its closed end, widens a little, the device may preferably be ovoid shaped, with one end having a wider diameter than the other end. The wider end serves to prevent the device from falling out and serves as an example of said means to promote retention of the device within the vagina. When the subject inserts the device, she deliberately relaxes the pubococcygeal muscle near the entrance to the vaginal vault. Once inserted into the widened cavern in the depth of the vagina, the device is prevented from falling out by the normal tension of the pubococcygeal muscle. Other designs are possible that can serve to retain the device in the vagina. For example, one can design it after the contraceptive diaphragm which is of disc shape and has a spring like rim that serves to keep the diaphragm in place once inserted. In accordance with the foregoing the means for easy insertion may merely be a smooth surfaced and a rotund body, or a flexible disc with a spring rim. The former is strongly preferred.

The housing material needs to be non-toxic and bio-compatible to not cause irritation or vaginitis. The material should be able to resist the detrimental effects of the vaginal acidity. Any metals used in contact with the acids should not act like a battery or be subject to metal deposits. Medical grade silicone rubber would make a good material.

Means for easy removal of the device may merely be a pull cord attached to one end (the narrower end) of the device which the user can grasp with her fingers to pull. Such a pull cord may be made of durable, bio-compatible material like nylon. The texture of the cord should not be irritating to the vagina or allow harboring of organisms. Instead of a pull cord, the device may have a ring-like tab which can be hooked by a finger. Other designs would be obvious to those skilled in the art.

The device when not inserted in the vagina can be kept in a water-tight container holding a disinfectant solution. A magnet at one end of the container switches off the device.

The device is preferably inserted into the vagina when the subject to be monitored is going to sleep, which for most people would be at night. The program followed by the microprocessor looks for the lowest temperature recorded once the device and its sensor reaches body temperature after being turned on for the night. Generally, the core body temperature drops to the lowest point between 4 to 6 A.M. when the body is most at rest. The computer rejects temperature less than 96.0 degrees F. as being unphysiologic. Recording of such a low temperature would indicate that the device fell out of the vagina. The lowest temperature recorded not rejected by the computer for reasons as just given would be stored in the microprocessor as that evening's basal body temperature BBT).

As the subject monitors the BBT daily, the microprocessor accumulates BBT data over a period of a few weeks. The microprocessor can be programmed to send to said display means a read-out informing the user as to where in the menstrual cycle the user is on any given day, e.g., "+3" would indicate 3 days after ovulation, especially after the computer has recorded at least one menstrual cycle of the user. The accuracy with which the computer can detect the time in the menstrual cycle improves with recording of more cycles, as the device gets acquainted with the user. After one to two cycles, it becomes possible to predict ovulation about 12 to 24 hours in advance and after 3 to 5 cycles, it becomes possible to predict ovulation about 3 to 7 days in advance. The program takes into consideration unusual happenings, such as when the user goes to bed much later than usual or when the user has a febrile illness. Such unusual temperatures are accounted for in predicting ovulation. The device is capable of interfacing with a larger external computer like the IBM PC or the Apple McIntosh/11 either thru a port accessible when the housing is opened as for a battery change or thru an external port. The device can also interface with a small hand-held or pocket computer like those readily available from Texas Instrument, Hewlett-Packard, and Casio, among others.

Figure 3:
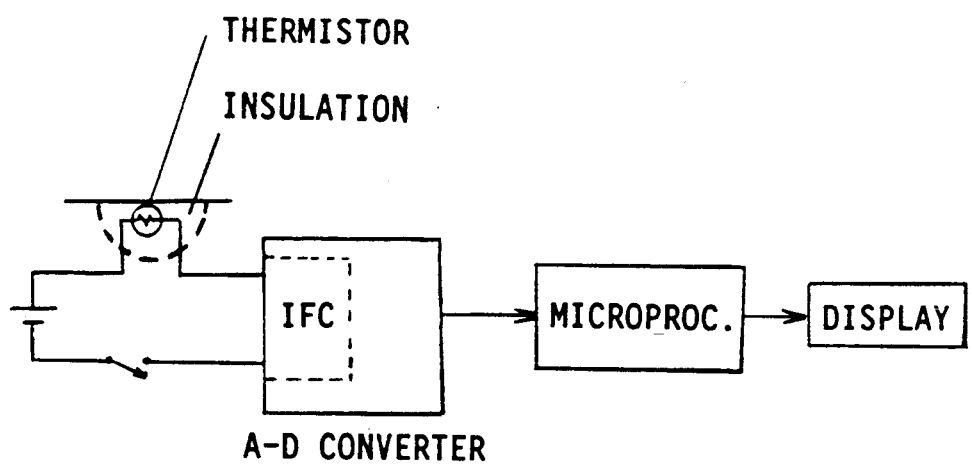
FIG. 3 is a schematic diagram of a basal body temperature monitor showing the core components and their relationship to each other.

BBT DEVICE, TYPE 2. Another version of body temperature monitor measures at the skin surface. Monitoring of the temperature at the skin surface is fraught with problems to the uninitiated. Depending on where on the body one places the sensor, one can get variations in recorded temperature of more than 5 degrees F. The temperature at many areas of the body e.g., wrists and feet, can be affected by the ambient temperature of the room. When the room is cold, circulations to extremities decrease and distal areas become quite cool to touch. Some areas of the body reflect the core body temperature more reliably. For example, the axillary temperature is generally about one degree F. less than the core body temperature (i.e., vaginal or rectal) However, an area like the axilla near the axillary artery is not subject to fluctuation in temperature like the distal extremities and is the preferred site for monitoring. The neck near the carotid circulation and the forehead, as well as the femoral triangle near the femoral circulation are other possible sites but less desirable ones. If the subject is wearing an insulating material over the trunk area (not a negligee that allows much air to circulate under it but a thermal underwear plus a pajama, for example), a sensor under this wide area of insulation can measure temperature which more closely reflects the core body temperature. The key is insulation to prevent room (and bedding) temperature from affecting the measurement at the skin. Specifically, then, the second version of a temperature monitor (FIG. 3) comprises: temperature sensing means; an analog to digital converter connected to convert analog signal from said sensing means to digital signal; a microprocessor means connected to said converter to record and microprocess data from said sensing means; a small battery powering said sensing means, said converter, and said microprocessor; a switch intermittently turning on and off certain power drawing circuits; discoidal housing to hermetically seal and contain said means and device components, one flat surface of said discoidal housing shaped and so disposed as to mold and seal over the skin of a body part and of surface area of at least 4 square centimeter, the temperature sensor apparatus of said sensing means being proximate to a thin heat-conducting material integral with said housing in the center of said discoidal skin-contacting surface; an insulating material surrounding said temperature sensing apparatus and said skin-contacting surface, said insulation being sufficient to allow the skin adjacent to said sensor to be sufficient to allow the skin adjacent to said sensor to fluctuate reflectingly of the core body temperature.

Figure 4:
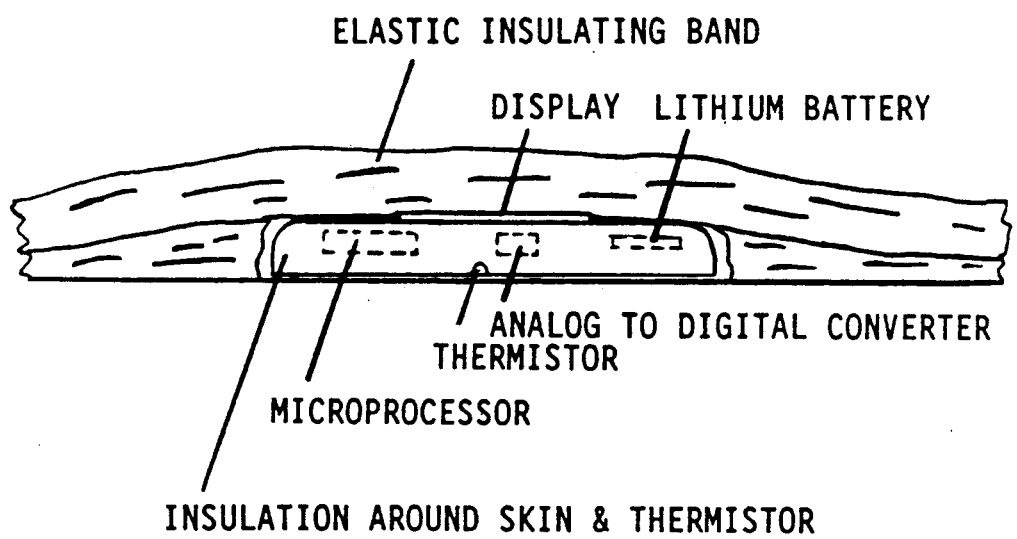
FIG. 4 is a cross-sectional schematic view of a body temperature monitor for measuring temperature at the skin of a subject.
Figure 5:
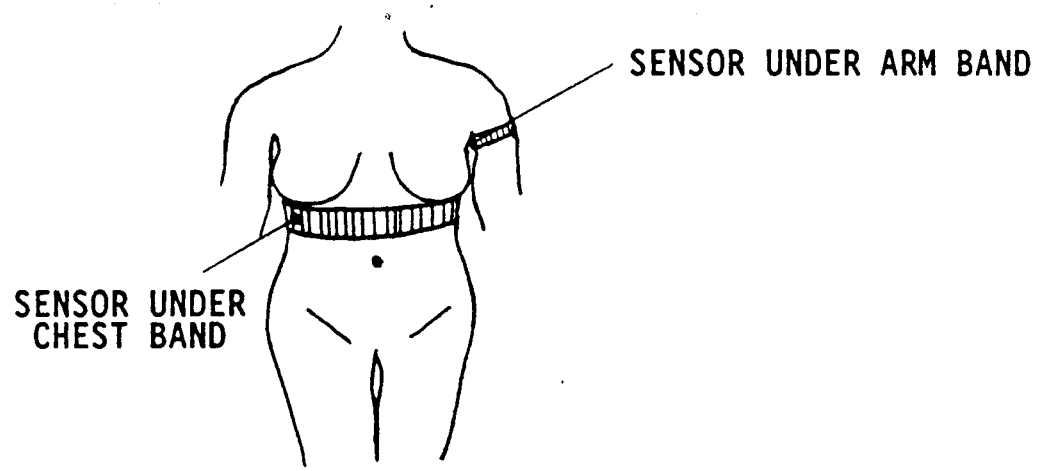
FIG. 5 is a drawing of a subject showing two sites at which the device of FIG. 3 can be used, held against the skin by an insulated, elastic band.

I found it to be very helpful to provide the skin being monitored with at least 4 square centimeter of insulation around the center of the skin sensor apparatus. Just as one finds the area under one's wrist watch to be warmer than the adjacent skin of the wrist and the forearm, an insulated area is (1) allowed by the autonomic nervous system to receive more circulation and 2) less subject to being cooled or heated by the environment; therefore, the insulated area reflects more closely the core body temperature. It is important that the insulated surface and the area proximate the sensor apparatus make a close seal with the skin in order to provide absolute insulation for the skin surface. A hypoallergenic adhesive, like that used on Nitro-Dur (R) Transdermal medication patch (Key Pharmaceuticals, Kenilworth, NJ), can serve a useful purpose in ensuring this contact although other means such as an elevated surface around the perimeter of the contact surface can help seal the contact area if an elastic band is used to keep the skin in contact with the device. Such a band can be useful when using the device in the axilla (FIG. 4). A 2-inch wide elastic band with additional insulation can be placed around the waist or around the lower chest (beneath the breasts) under which the monitoring device can be held against the skin (also FIG. 4).

In one improvement of the second version, a second temperature sensing means is employed wherein the second sensor apparatus is placed on top of the insulating material covering the first sensor so as to enable the second sensor to measure the temperature of the surroundings. The second temperature sensing means also feed data to said microprocessor via an analog to digital converter. The use of the second sensor enables one to reduce the skin contact area and the extent of the insulation because sensing the surrounding temperature enables the microprocessor to compute an adjustment to the temperature measured at the skin. Through empirical tests, one can compute the amount of cooling on the skin effected by cooler environmental temperature. Through such a test, one can develop a table (see sample Table I) which relates core body temperature to measured temperature at a location in the body to ambient temperature surrounding the location.

The use of the second temperature sensor permits monitoring at the wrist which is subject to the most extreme fluctuation in temperature. In the case of empirical tests for the wrist unit, one is not merely accounting for the cooling effect of the environment but the body's autonomic response in decreasing circulation to an extremity when such an extremity is exposed to cold to prevent loss of heat from the body.

The method of my invention then, in respect to the temperature monitoring function, is a way to monitor the core body temperature comprising: monitoring the skin surface temperature at a location of the body and monitoring the ambient temperature surrounding the skin at said location; adjusting the temperature measured at the skin surface by said ambient temperature using an experimentally derived table that correlates core body temperature to skin surface temperature measured at said location as a function of said ambient temperature.

If one measures the skin surface temperature at Location A on the body as 95.80 degrees F., and if the ambient temperature surrounding Location A is measured to be 78.0, by using sample Table I, one can determine that the core body temperature is 98.1. In practice, a computer makes these correlation using the data such as in Table I.

In summary, by monitoring ovulation, the devices I have described can improve fertility by pin-pointing the best time for coitus to achieve conception and the device can also be used to avoid conception by timing sexual intercourses away from such fertile periods.

When I began to develop a basal body temperature monitor, I initially developed in 1981 a device that separated the temperature sensing means from the microprocessor. The sensed temperature data were transmitted using a National Aeronautics & Space Administration (U.S.A.) (NASA) telemetry system (Report SP-5094, "Implantable Biotelemetry Systems," 1970) over an FM channel. I decided in the end that this approach, in large scale consumer use, may be found to be fraught with problems of unreliability when used outside the environment of carefully conducted research. More recently, I have heard that others have become interested in a system like the one I developed almost a decade ago. However, I do not believe it will be possible to build a more reliable system than that described in the present application, if one uses a telemetry system, even with greater skills of others. I do claim priority on such wireless devices anyway and indeed have copyrighted software applicable to such devices.

As a final note on the temperature monitoring function, I would like to add that the wrist unit with dual sensors can also incorporate watch (time-keeping) functions. The wrist watch units are designed to be used by men as well as women, not only for monitoring of ovulation, but for monitoring of daily body temperature. While day-time temperature fluctuates substantially (rising when exerting physically or when under stress), there are periods when the temperature returns to the baseline level (i.e., the temperature of a body at rest). When the subject wears such a monitor for a period of weeks, the computer "learns" the normal pattern and can detect deviance from the "norm" when the monitored subject is becoming ill. I have discovered that continual body temperature monitoring can be the earliest detector of diseases, including cancer (I am not referring to just a general elevation in temperature). One sees characteristic 24 hour temperature curve for various diseases, not just for TB, malaria, and other infectious diseases, about whose temperature patterns are already well-known. I envisioned a device that would be worn by virtually everyone. To this end, I have worked hard at developing a device that would be simple enough to use to be "consumer-acceptable." I take the credit for being the first to recognize the potential diagnostic importance of continual body temperature monitoring and in developing the means to accomplish this through a wrist monitor, which I believe is the only "consumer-acceptable" way that is still reliable and economical. A suitable device can be marketed for under U.S. $10.00.

CARDIAC ISCHEMIA MONITOR

Figure 6:
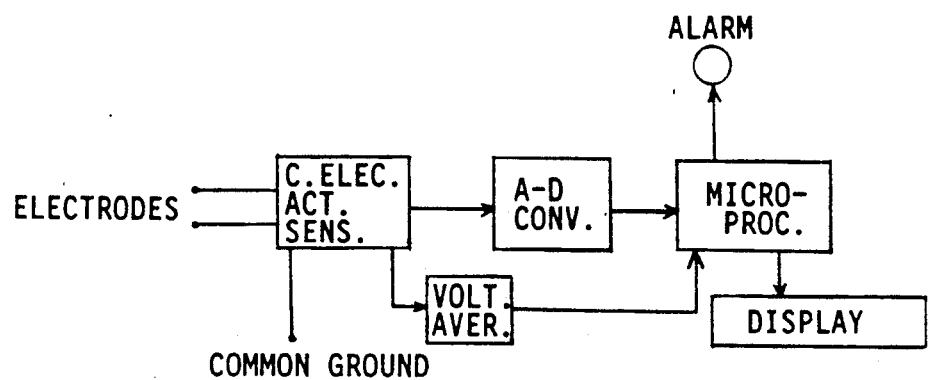
FIG. 6 is a schematic diagram of the device for detecting and warning a user of an impending heart attack, showing relationships of various components.

The cardiac monitor portion of the device I have invented comprises (FIG. 6): means for sensing the electrical activity of the heart at the skin surface; a voltage averaging means connected to said sensing means to average the voltage potential sensed by said sensing means; analog to digital converter means connected to said sensing means to convert the analog signals from said sensing means into digital signals; a microprocessor connected to said averaging means and to said converter to record and microprocess data from said averaging means and said sensing means; an alarm connected to said microprocessor to be triggered by said microprocessor according to specific criteria; display means connected to said microprocessor providing interpretation of electrical cardiac activity being sensed; a battery powering said electrical activity sensing means, said voltage averaging means, said analog to digital converter means, said microprocessor, said alarm, and said display; a durable, light-weight housing within which to hermetically seal all said means and device components.

Figure 7A:
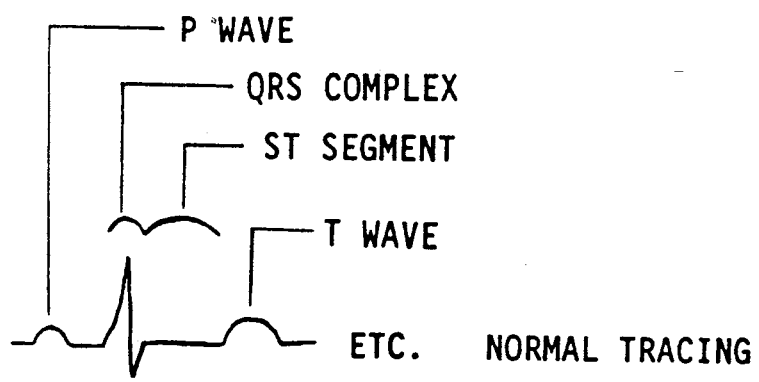
FIGS. 7A is an example of normal electrographic tracing and FIG. 7B is an example of an electrocardiographic tracing from a patient about to have a heart attack, showing two indicators of the impending attack, viz., (1) a change in average voltage potential over one pulse cycle due to so-called ST segment changes and (2) an increase in the frequency of premature ventricular contractions (PVC).
Figure 7B:
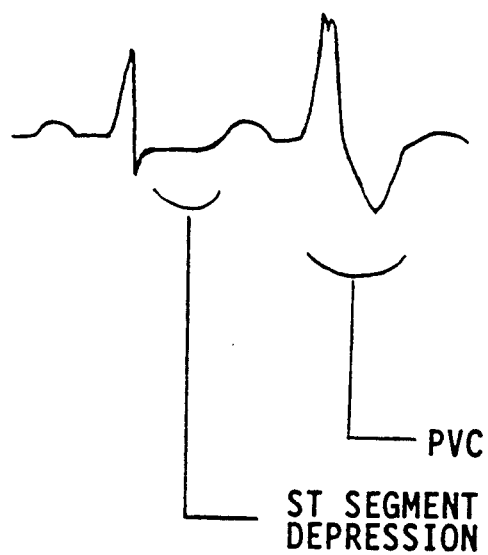

There are warning signs evident in the electrocardiograph (EKG) tracing of an impending heart attach victim (FIG. 7B). These contractions (PVC's) and so-called ST segment depression. "Heart attacks" are caused when an artery feeding oxygen to a group of heart muscles become blocked by arteriosclerotic plaques and a blood clot. The blockage in circulation results in the death (infarction) of that group of heart muscles (myocardium). Often the myocardial infarction begins in a small area and if no contravening steps are taken, the area of infarction enlarges. It is, therefore, important to be able to detect impending or early heart attacks so that a monitored subject can take lifesaving steps to prevent advancing his status into a deadly, large infarction. Once the infarction begins, more changes in EKG occur (e.g., appearance of the Q wave, ST elevation). A textbook on EKG interpretation describes these changes well and so I will not repeat them here. The two important things are: (1) the average voltage of the routing contraction changes as an artery becomes blocked (the "average voltage" is the average calculated by adding the voltages of one cycle of non-premature, routing contraction and dividing the sum by the number of addend —the change in the average voltage reflects the change in the ST segment and other part of the EKG tracing; and (2) frequency of PVCs increases (PVCs are easily distinguishable from a routing pulse because a PVC is not preceded by a small wave called the p wave, PVC occurs outside the usual time interval between pulses, and the average voltage of a PVC is markedly different from a routing pulse). The microprocessor interprets the increase in PVCs and/or the changes in the average voltage of a heart cycle and causes (1) an alarm to be sounded and (2) a pre-programmed message to be displayed, warning the user of a possibly impending (increased frequency of PVCs, ST segment depression changes) or an early heart attach (Q wave, ST segment elevation (depression in case of posterior ventricular wall infarction when monitored at anterior chest).

Means for sensing electrical activity of the heart can be the standard ones used in various portable cardiac monitors commercially available. Wireless monitors can be like that described in the NASA publication (ibid.)

Said means for sensing the electrical activity of the heart at the skin will produce an analog signal which can be fed to means for averaging the voltage. The original analog signal from the sensors can be converted by an A-D converter to a digital signal and both signals from the converter and from the averager can be fed separately to a microprocessor. The microprocessor itself can act to average the voltage of any cycle of contraction or of the QRS complex, although using a hardware voltage averager would require less memory in the microprocessor.

In an advanced version of the device, the wearer can phone his/her doctor, push a button on the monitor and transmit the EKG recording being made by the monitor through the telephone by having the monitor broadcast a continuous audible tone which fluctuates with the voltage, much like it is routinely done with large EKG machines. In such an advance device then, in addition to above means and components, the device would also comprise a loud speaker means, amplifier means between said sensing means and said speaker means to amplify the small voltage sensed by cardiac electrical activity sensing means into larger ones sufficient to drive said speaker, and a switch to cause the monitor into or out of the mode of broadcasting the EKG. Amplifier means are those routinely used for amplifying small voltages into larger ones that can drive the speakers.

Instead of a voltage averaging means, it is possible to use a more complex microprocessor program to analyze the EKG being monitored more specifically for other changes in the electrical activity that signify an impending or early heart attack. Therefore, in another embodiment, a more powerful microprocessor capable of handling a more complex computer program is employed. Software capable of discriminating the changes in the EKG would be obvious to those skilled in the art. Once the microprocessor decides that the monitored subject is about to have or is having a myocardial infarction, it can cause an alarm to sound and display to read, for example, "warning: cease the stressful activity you are engaged in, proceed to an emergency facility at once." Such a display may be a liquid crystal display.

There is a wrist watch-like, EKG-based, pulse monitor called "HeartWatch (R) (Computer Instruments Corporation, Hempstead, NY) which senses electrical activity of the heart via chest sensors, whose signal is transmitted without wires to a wrist watch-like microprocessor. Such a device can be adapted for use in the present invention as the means for sensing the cardiac electrical activity. Other components (namely, voltage averager, A-D converter, microprocessor, alarm, and display) of my invention can be fitted into a case not unlike that of the commercial monitor.

In the case of the HeartWatch (R), there is an elastic band which is worn around the chest that holds three electrodes over anterior chest (one serves as a common ground to deal with environmental electrical activity in the room the subject is in, e.g., 60 Hz AC cycle), from which the electrical activity can be sensed. The sensed electrical activity is transmitted to the wrist device. (I would like to note that reliable transmission of EKG readings to a remote receiver using frequency modulation was first developed by National Aeronautics & Space Administration (U.S.A.). I cite again for reference NASA report SP-5094, "Implantable Biotelemetry Systems," 1970.)

As an additional embodiment, the wrist device may have a reservoir for various cardiac medications, such as anti-arrythmic lidocaine or atropine, and an infusion pump that can administer any of these medications according to the microprocessor program (lidocaine for evidence of increased cardiac irritability as reflected in frequent PVCs; atropine for drop in pulse rate below 50 after an infarction). These drugs can be administered via a fine needle which can emerge and penetrate the subject from the undersurface of the wrist unit. The "firing" of the needle can be electrically activated by the microprocessor using a standard magnetic drive. Instead of a needle, the drug can also be administered via skin absorption when the pump infuses the drug onto an absorbent pad on the undersurface of the unit in contact with the skin, especially when carriers are sued that facilitate skin absorption of drugs. An example of such carriers is dimethylsulfoxide(DMSO). It is well-known that when drugs are mixed with DMSO and applied to the skin, the drugs are absorbed rapidly. Judiciously and timely applied, these cardiac medications save lives.

Since I invented the above device nearly a decade ago, I recently heard after writing the above descriptions that others have been developing portable cardiac monitoring devices using sophisticated microprocessors and that one such a monitor even sounds an alarm when suspicious ST segment depression is detected. These are apparently meant to be employed by very sick heart patients at high risk for heart attacks. Presumably, these units must be large and cumbersome and style after the old Holter-monitor which we physicians placed on ambulatory patients to record their heart activity over a 24 or 48-hour period. These portable monitors of others are not at all the kind of devices I envisioned for the masses. Substantial numbers of fatal heart attacks occur in people who never knew they had a heart condition. For many, their first attack is their last. People who feel perfectly healthy are not going to use anything cumbersome. At mot, they would be willing to wear a chest band holding cardiac sensors, particularly when engaging in stressful activities, like sports or certain business meetings. My invention, then, is a cardiac monitoring device that is aesthetically-pleasing, user-friendly, lightweight, and non-obtrusive. The microprocessor, voltage averager, A-D converter, battery (battery for the sensors is housed with the sensor), alarm, and display are all housed within a unit that resembles a wrist watch and, in fact in an advantageous embodiment, is also a wrist watch (The HeartWatch (R) described above, indeed, is also a wrist watch.) The use of voltage averaging as the means for detecting changes in biological activity, in this cardiac monitoring function and the glucose monitoring function to be described below, is my invention and is key in creating a light-weight, economical device. The sue of hardware voltage averager makes the device even more simple and almost eliminates the need for the microprocessor. For example, voltage averaging can be triggered by the p-wave, for the time duration between the end of p wave and the end of the t wave (e.g., 0.4 second). Similarly, PVCs can be detected also without sophisticated microprocessors using hardware counters of voltage pulses.

Figure 8:
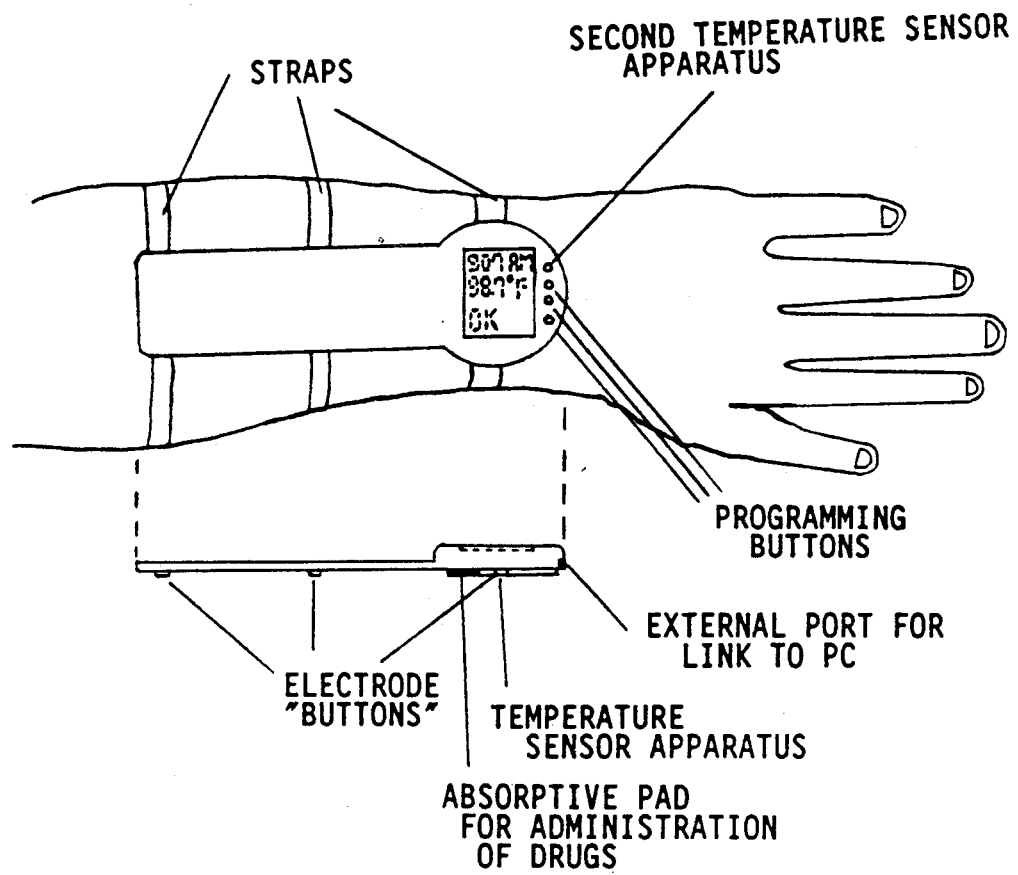
FIG. 8 is a perspective view of the integrated multifunctional CAMBY unit which resembles a wrist watch and is mounted on the wrist. It detects cardiac electrical activity through its three electrodes strategically placed on the main body and the tail of the unit. It detects correct body temperature through its temperature sensing apparatus on the skin-contacting surface and on the upper face of the unit. The wrist unit receives data about the body fluid glucose level from a remote glucose sensing unit capable of wireless transmission. A microprocessor and voltage averager interpret data provided them from sensing means and displays informational read-outs about the status of the body. The wrist unit is able to communicate with a desk-top personal computer via its external port. The microprocessor can cause the transmission of instructions to a remote insulin pump in the event the glucose level in the body is too high. The microprocessor can also cause the administration of lifesaving cardiac medications through a skin-contacting absorbent pad.

In keeping with my requirement that the device be aesthetically pleasing, one advantageous embodiment of my invention is a system in which the cardiac electrical activity sensor is located entirely in a small wrist-watch like device (FIG. 8). People are more prone to wear a "wrist-watch" than a chest band. The electrodes in the wrist unit are located on its under-surface using contact-enhancing "buttons" like those found on the chest sensor of the HeartWatch (R). Especially unique is the manner in which this unit measures electrical activity. The dimension of the wrist device is approximately 12.7 cm long, 2.54 cm wide. The device is held on the upper wrist-lower forearm area by three straps, located about equal. distances from each other. The "button" electrodes are in contact with the skin at the location of these straps. The electrode at the wrist serves as the common ground. As the electrical voltage generated by the heart travels down the arm, ti is first detected by the electrode most proximal to the hear and then, after a delay, by the second electrode, in the middle of the unit. These two separate electrical tracings can be electronically subtracted from each other leaving a tracing which when amplified reflects the electrical activity of the heart. While such a tracing does not resemble the usual EKG tracing, an ST segment depression can be seen in the subtracted tracing as a characteristic change that alters the average voltage of a pulse cycle. Other parts of this wrist device, including connections between the sensors, voltage averager, microprocessor, display, alarm, and the battery, are as already described. With advances in electronics, especially in speed, it will be possible to make the device shorter and more the dimension of a wrist watch.

The overall dimension given above for the wrist unit is advisable but depending on the shielding capability and speed of the electronics used, variation is possible from them. What is important is: that there be three electrodes, two sensing and one common ground; that all the electrodes be placed at different distances from the heart on the forearm. There are advantages in placing the ground electrode at a greater distance from the heart than the two sensing electrodes. Means are provided to allow continual subtraction from each other of the electrical potentials sensed at the two sensing electrodes, whose difference is the potential that is amplified and fed to said voltage averager and said microprocessor as a digital signal.

A wrist device as described above can be useful not only to detect acute cardiac ischemia (relatively sudden change) but also to detect, warn, and medically treat cardiac arrythmia. The treatment can be by medication as described or via wireless triggering of an implanted ventricular defibrillator, many types of which are now commercially available.

One method of my invention then, in respect to the cardiac monitoring function, comprises: sensing cardiac electrical activity at an extremity using two sensing and one common ground electrode wherein each said sensing electrode is placed at different distances from the heart; subtracting the electrical potential sensed at one sensing electrode from the electrical potential sensed at the other sensing electrode; microprocesssing said subtrahend over time to screen for a change reflective of acute cardiac event.

GLUCOSE-SENSOR/BIO-ARTIFICIAL PANCREAS

I am the inventor of the bio-artificial liver and the bio-artificial pancreas (U.S. Pat. Nos. 3,734,851 and No. 3,827,565). These are devices, currently in final clinical trials, which work on the principle of flowing blood to be treated across a surface of a semi-permeable membrane which separates the blood from liver or pancreatic islet cells positioned on the other side of the membrane. In the case of an implantable bio-artificial pancreas for treating a diabetic with high blood sugar, it is a tube-like device which is connected into the circulation of the diabetic. The tube is made of a semi-permeable membrane and islet cells are placed on the outside surface of the tube; there is a casing that surrounds the islet cells and the tubing so that the islet cells do not come in direct contact with the diabetic's blood or tissue. The semi-permeable membrane keeps the islet cells from washing away into the circulation and prevents the diabetic's lymphocytes and anti-islet antibodies in the circulation from attacking the foreign islet cells.

I have developed a glucose sensor that uses the bio-artificial pancreas. The device (FIG. 9) comprises the following: a semi-permeable membrane; islet beta cells proximate to one side of said semi-permeable membrane; means for sensing electrical activity of beta cells; housing means to seal-in beta cells and electrode assembly proximate said beta cells, said electrode assembly being a part of said sensing means; an analog to digital converter connected to said sensing means to convert the analog signal from said sensing means into digital signal; a microprocessor connected to said converter to receive digital data from sensing means; and a display means connected to said microprocessor displaying a read-out from said microprocessor about insulin secreting activity of said beta cells. Such a device is surgically glued or stitched in place adjacent body fluid to be treated so that said semi-permeable membrane is in contact with said body fluid. If abnormally high level of glucose is present in the body fluid an abnormally high amount of glucose diffuses across said semi-permeable membrane and triggers said beta cells to commence secreting insulin. Secretory activity of said beta cells causes a characteristic electrical activity in said beta cells which can be detected by a microelectrode proximate said cells, said microelectrode being connected to a buffer amplifier and then to an amplifier and referenced to a reference electrode away from said cells. (For details about the changes in the electrode potential of beta cells during insulin secretion, see "Membrane Potential of Beta-cells in Pancreatic Islets" by H. P. Meissner and H. Schmelz. Pflugers Arch. (1974)351: 195-206; "Electrical Characteristics of Pancreatic Islet Cells" by E. K. Mathews and Y. Sakamoto J. Physiol. (1975), 246: 421-437; and earlier articles by E. K. Mathews cited in the 1975 article.) The analog signal of the electrical activity can be converted to a digital signal by an A-D converter and fed to a microprocessor which can discriminate and interpret the electrical activity. In the most simplest program, the microprocessor can discriminate the sudden change in average voltage potential measured by the electrode proximale beta cells when the beta cells commence secretory activity (FIG. 10B). Using a more complex computer program, the frequency of plateau phases are counted. Abnormal glucose levels are detected in a higher frequency. The plateau phase's spikes themselves also indicate glucose level—the spike frequency rises with higher abnormal levels of glucose. A sophisticated computer program can therefore read the level of glucose from counting the spikes over time during the plateau phase. Actually, one can accomplish these interpretations without a complex computer program by using certain harware, such as a voltage window discriminator (that allows current to pass only between certain voltages) and a counter of such passages. Microprocessor decision that a secretory activity is occuring can be indicated at the display means which may simply be a liquid crystal display. In a further embodiment of the invention, a pump for infusing insulin into a diabetic from a reservoir is utilized which is controlled by said microprocessor. The microprocessor triggers the pump to infuse insulin at a pre-programmed rate whenever the microprocessor detects beta cell secretory activity. If a more complex computer program is used so that the computer can detect the degree of abnormality of glucose level, the pump speed can be raised according to how high the sugar level is. While the insulin secretory sensing apparatus holds only a few thousands to a few hundred thousands of beta cells whose total output of insulin is grossly insufficient to lower the high blood sugar in a diabetic, allowing the artificial pump to mimic the beta cells secretory activity permits substantial amounts of insulin to be infused into the diabetic to correct high blood sugar levels. One then has an effective closed-loop artificial pancreas. Where said microprocessor interfaces with a pump, said display means may be omitted. When said microprocessor interfaces with said display means, the device can act as a detector of body fluid glucose level which is abnormal to said beta cells.

A suitable pump is readily available from many sources. One pump that is microprocessor controlled has been developed and publicized by the John Hopkins University (Bethesda, MD).

The semi-permeable membrane's requirement has been discussed in my bio-artificial pancreas patent application. Essentially, it is preferably a microporous membrane with porosity not exceeding 0.45 microns which prevents cross-over of immunologically active cells. For example, it can be of polycarbonate, 10 micron thick, with or without an anti-thrombogenic coating with ultra-low-temperature isotropic carbon (CarboMedics, Inc., San Diego, CA; See "Oxygen Permeability of Carbon-surfaced Microporous Membranes", by H. A. Borovetz, J. of Biomed Materials Res. (1980) 14:145–154). Other methods such as heparin bonding on the membrane can be used to discourage blood clots from forming on the membrane. Another method to discourage blood clot formation is to place adjacent to and mixed with the beta cells, heparin secreting mast cells obtainable from the peritoneum by standard methods (see "Modulation of Cyclic AMP in Purified Rat Mast Cells" by Timothy Sullivan. J. of Immunol. (1975) 114(5): 1473–1479). Such mast cells can and can be made to secrete heparin keeping the membrane area anti-thrombogenic.

Figure 9:
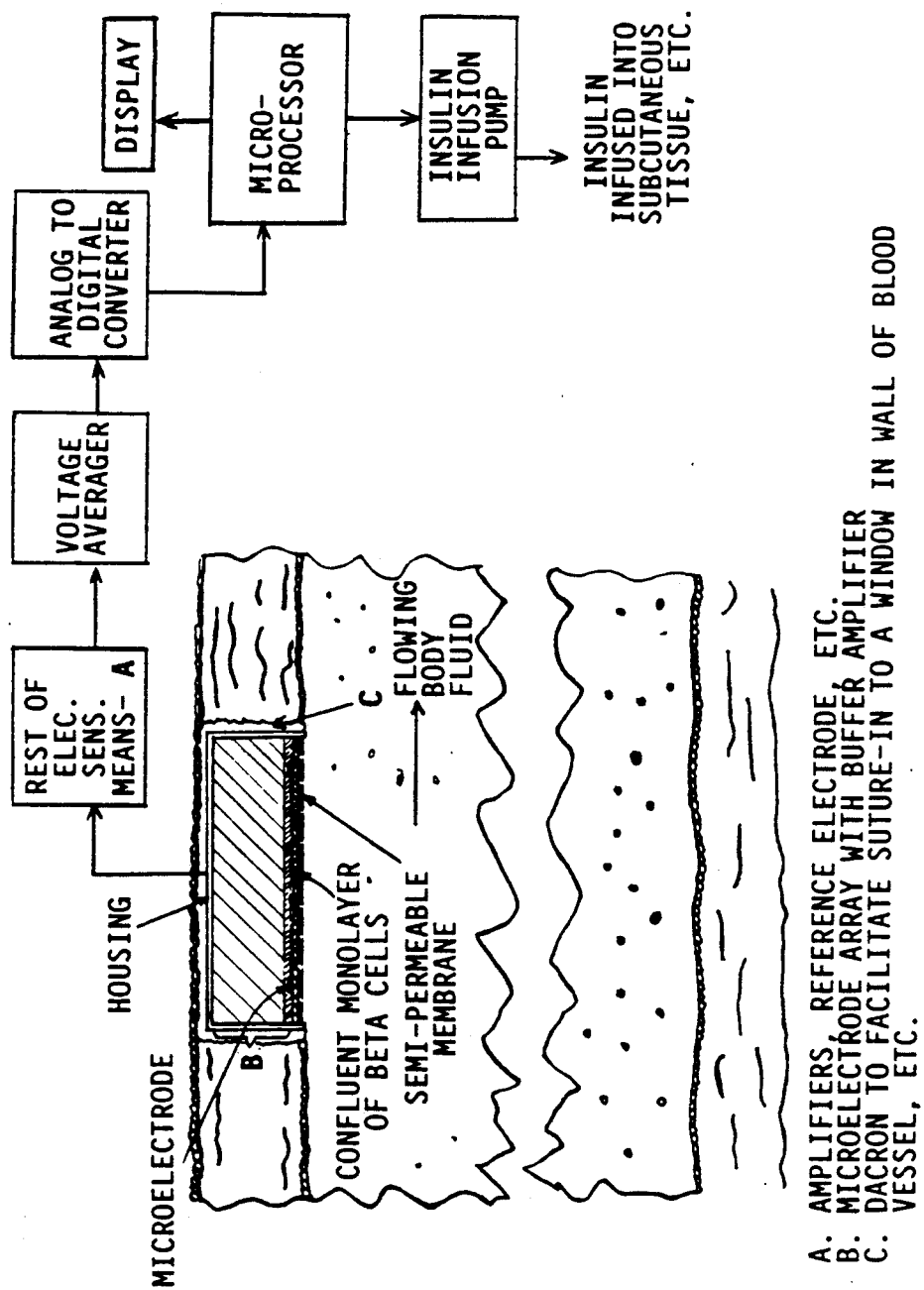
FIG. 9 is a cross-sectional view of glucose sensor apparatus and a schematic diagram of the other associative components showing their relationships to each other.
Figure 10A:
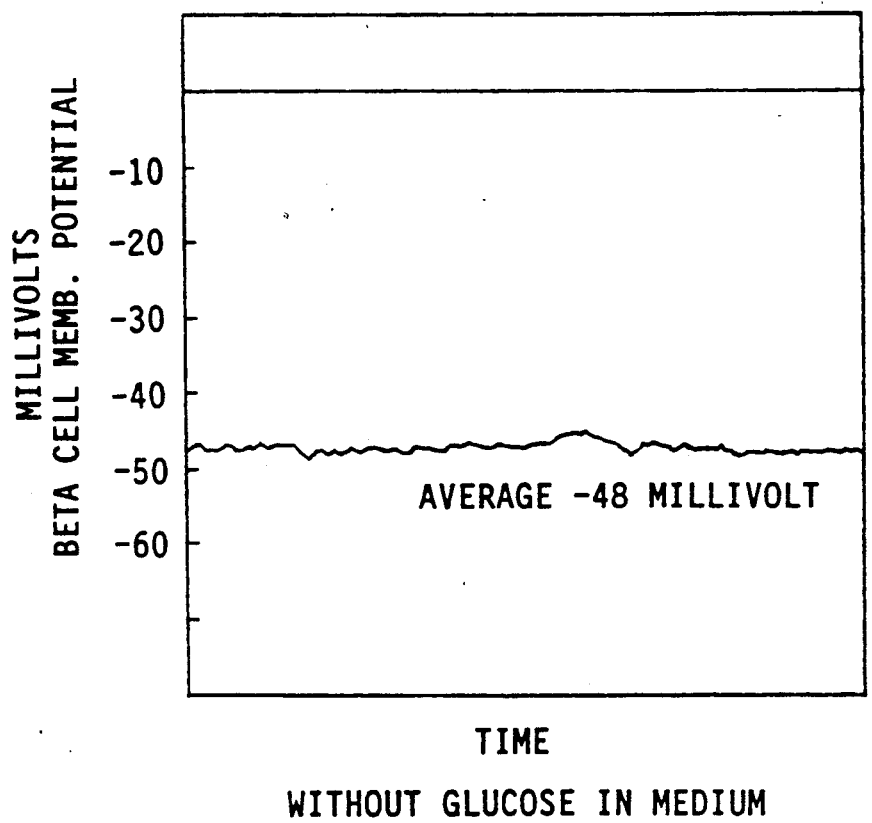
FIG. 10A shows electrical activity measurable from Islet (of Langerhans) beta cells exposed to normal level of blood glucose and FIG. 10B shows the changes in electrical activity measurable from Islet (of Langerhans) beta cells when beta cells are exposed to abnormally high amounts of glucose, the specific changes being an alteration of the average voltage potential, an increase in plateau phases, and an increase in spike frequency during plateau phases.
Figure 10B:
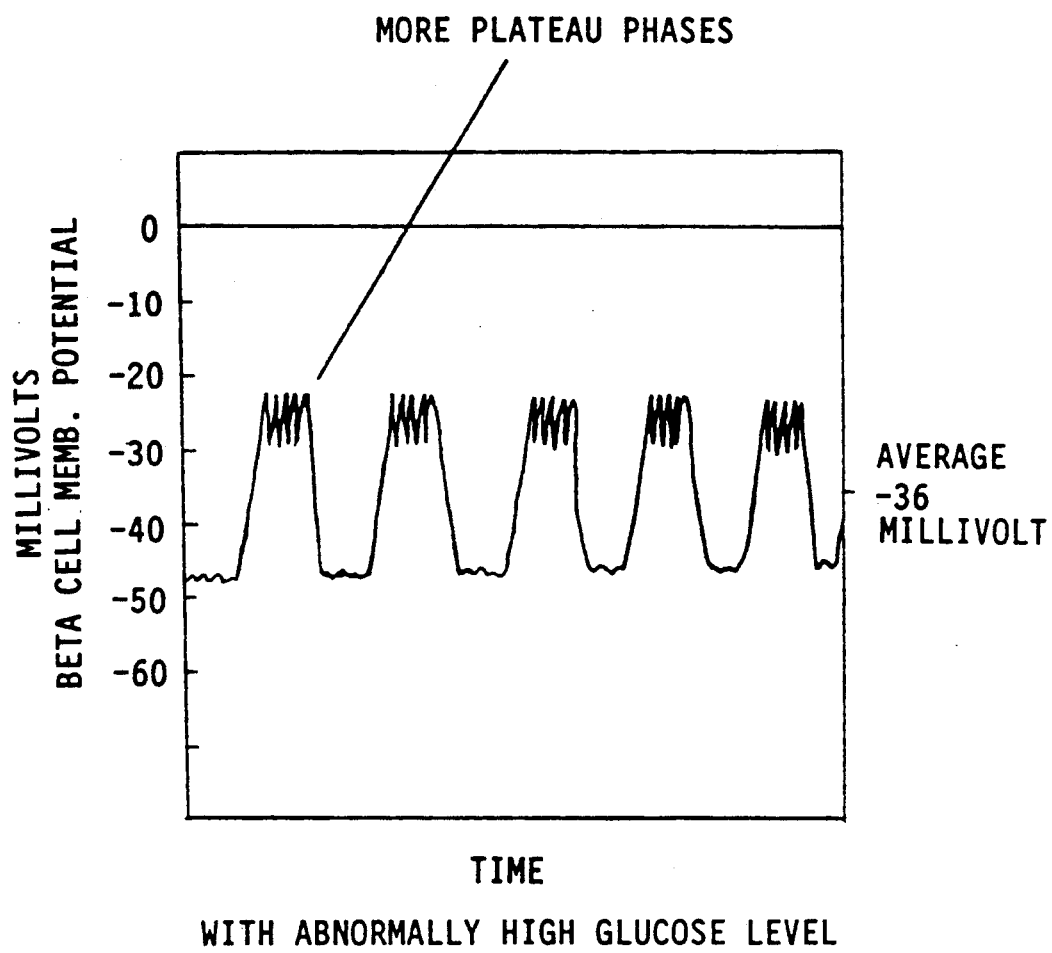

As shown in FIG. 9, the semi-permeable membrane, the adjacent beta cells and the microelectrode array may be stitched or glued into a window surgically created in a blood vessel wall, the peritoneal wall, or wall of other cavities in which the cavity fluids are engaged in rapid dynamic equilibrium exchange with the rest of the body fluids of the monitored subject. The membrane can also be part of a small needle wherein most of the needle are made of a bio-compatible stiff plastic (may be reinforced by metal except for a small window on one side in which the device can be placed well insulated from any adjacent metal, with the semi-permeable membrane in line with the exterior of the needle so as to allow the glucose sensor to sample the extracellular fluid adjacent to the needle. The needle may be placed into a blood vessel, a body cavity, intramuscularly, or even subcutaneously, although the latter site does not exchange its fluids as rapidly with the rest of the body and there will be some delay in the way the glucose level changes subcutaneously in response to the changes in the glucose level in the rest of the body fluid. A computer program can account for this delay so that insulin is not continued to be pumped out when the blood glucose level has already become low in response to the insulin pumped out earlier.

Suitable beta cells are isolatable in purified form by many well-known methods Beta cells isolated by methods like those of Chick (William L. Chick, "Pancreatic Beta Cell Culture: Preparation of Purified Monolayers," Endocrin. (1975) 96: 637–643 or Scharp (David Scharp, "Isolating the Elusive Islet," Diabetes (1980) 29(1): 19–30) can be further purified using known methods like cell separators (e.g., Cytofluorograph, Ortho Diagnostic Systems, Inc., Raritan, NJ) and density gradient centrifugation.

By the term, "means for sensing the electrical activity of beta cells," I mean an assembly like that described by D. T. Jobling et al. ("Active Microelectrode Array to Record from the Mammalian Central Nervous System in vitro", Med. & Biol. Eng. & Comput. (1981) 19: 553–560) which is capable of sensing electrical activity of cells extracellularly without an intracellular glass micropipette electrode.

Advances are being made in transplanting immunologically mis-matched tissues from one person to another and I expect that better immunosuppressant drugs and methods will be developed which will allow such transplants. When such a day arrives, it may become unnecessary to use the semi-permeable membrane. The scope of my invention includes a device which does not use a semi-permeable membrane. What will be important is that a beta cells be placed proximate to an electrode and more practically a layer of beta cells may be attached to a surface on which are etched electrodes. Such a layer would bathe freely in the body fluid. However, the necessity of a semi-permeable membrane that blocks the passage of antibodies (large protein molecules) may I5 continue because diabetics type I) appear to have auto-islet antibodies. Being able to transplant across histo-immunological barriers does not solve the problem of auto-immune antibodies. Furthermore, even if transplants become possible, one may still need a device like mine because in some Type II diabetics, their hyperglycemia is associated with higher than normal amount of insulin in their blood stream. These individuals have resistance to the action of insulin and require far more insulin than normal to keep their sugar value normal. Only an artificial device that can be made to infuse above normal amount of insulin can help such patients.

A method of my invention then, in respect to the glucose sensing function, comprises: placing pancreatic beta cells in contact with body fluid to be treated; providing means to sense the electrical activity of said beta cells in response to body fluid glucose level; microprocessing said sensed electrical activity to determine body fluid glucose level.

THE INTEGRATED MULTI-FUNCTION DEVICE

So far in this application, I have described the three functions of the CAMBY device. Needless to say, any two can be incorporated in a device without the third and a device can be made that is capable of only one function. However, it would be economical to combine several functions because one microprocessor can work with two or more functions. Having described each function in detail separately, I will now describe the integrated device.

The integrated device comprises;

I. The sensor systems -- A. temperature sensing means;
B. means for sensing the electrical activity of the heart at the skin surface;
C. a semi-permeable membrane; means for sensing electrical activity of beta cells; housing means to seal-in beta cells and electrode assembly proximate said beta cells, said electrode assembly being a part of said beta cell sensing means;

II. Analog to Digital Converter—an analog-to digital converter connected via multiple feed-in switch to said temperature sensing means, to said cardiac electrical sensing means, and to beta cell electrical sensing means, to allow analog signal from each sensing means to be separately converted, one at a time, to digital signal;

III. A microprocessor—a microprocessor means connected to said analog to digital converter to record and microprocess data from three said sensing means;

IV. A voltage averaging means—a voltage averaging means connected to said cardiac electrical sensing means to average the voltage potential sensed by said cardiac electrical sensing means;

V. Special provisions relevant to the temperature sensing means required to make it work, including a special housing, insulation around the temperature sensor apparatus, and the second temperature sensing means necessary to interpret the data from the first temperature sensing means—discoidal housing to hermetically seal and contain said temperature sensing means, one flat surface of said discoidal housing shaped and so disposed as to mold and seal over the skin of a body part and of surface area of at least 4 square centimeter, the temperature sensor apparatus of said temperature sensing means being proximate to a thin heat-conducting material integral with said housing in the center of said discoidal skin-contacting surface; an insulating material surrounding said temperature sensing apparatus and said skin-contacting surface, said insulation being sufficient to allow the skin adjacent to said sensor to be sufficient to allow the skin adjacent to said sensor to fluctuate reflectingly of the core body temperature; a second temperature sensing means wherein the second temperature sensor apparatus is placed on top of the insulation material covering the first sensor apparatus so as to enable the second sensor to measure the temperature of the surrounding, said second temperature sensing means also feeding data to said microprocessor separately via said multiple feed-in switch and said analog to digital converter;

VI. A small battery powering all power-drawing circuits including said temperature sensing means, said cardiac electrical activity sensing means, said beta cell sensing means, and said microprocessor;

VII. A switch intermittently turning on and off certain power-drawing circuits, except those affecting the memory of said microprocessor, to conserve battery;

VIII. An alarm connected to said microprocessor to be triggered by said microprocessor according to specific criteria;

IX. A display means connected to said microprocessor;

X. An insulin reservoir and pump controlled by connection to said microprocessor.

By the term "multiple feed-in switch," I mean any of the standard switches that, on the input end, allow connection to multiple sources, which permit a computer to have control as to which connection is active at any given time in allowing passage of electricity from a source to a single destination, in this case, an analog to digital converter.

Using telemetry means, it is possible to not house all of the above means and devices together connected by hard wiring. For example, the temperature sensor and cardiac activity sensor can be on the chest of a monitored subject and their data can be transmitted to a microprocessor-alarm-display unit on the wrist. Similarly, the glucose sensor and insulin reservoir/pump can be elsewhere on the body, its location being rotated daily, and the microprocessor can communicate with the sensor and the pump via wireless means. By wireless means, I means the type developed by NASA, described above. Therefore, when I use the work "connected", I include above types of connection or communication via wireless means.

In one embodiment of the integrated device, the temperature monitor is in its entirety within a wrist device, the cardiac monitor is also within the same wrist device, and the glucose sensor is i a remote location transmitting data to the microprocessor in the wrist device and the insulin pump is also located remotely receiving transmitted instructions from the same microprocessor.

Having described some of the best embodiments of my invention, I wish nevertheless to note that, to those skilled in the art, variations can be through of in the described device without deviating from the scope of my invention.

I claim:

1. Device comprising: an analogy temperature sensing means including a temperature sensor and means to generate an analog electric signal representative of the sensed temperature; an analog to digital converter to convert the analog signal from said sensing means to a digital signal; a microprocessor means connected to said converter to record and microprocess said electric signal; insulating material surrounding said temperature sensor to insulate said sensor from heat generated from said microprocessor means; a small battery powering said sensing means, said converter, and said microprocessor means; a switch means for intermittently turning on and off certain power drawing circuits; a switch means for turning on and off power drawing circuits; an externally controllable switch to enable said switch means from the outside of said device; said device hermetically sealed inside a durable, light-weight, bio-compatible rotund housing; means to promote retention of the device within a vagina; means to facilitate intravaginal insertion and removal.

2. Device comprising: an analog temperature sensing means including a temperature sensor and means to generate an electric signal representative of the sensed temperature; an analog to digital converter to convert an analog signal sensed by said sensing means to a digital signal; a microprocessor means connected to said converter to record and microprocess said electric signal; a small battery powering said sending means, said converter, and said microprocessor means; a switch means for intermittently turning on and off certain power drawing circuits; a discoidal housing in which said device is hermetically sealed, one flat surface of said discoidal housing shaped and adapted to mold and seal over the skin of a body part of surface area of at least 4 square centimeters, the sensor of said sensing means being proximate to a thin heat-conducting material integral with said housing in the center of said discoidal skin-contacting surface; an insulating material surrounding said temperature sensing means and said skin-contacting surface, said insulating material being sufficient to allow the skin adjacent to said sensor to fluctuate reflectingly of the core body temperature.

3. Device comprising analog sensing means for sensing the electrical activity of a heart at skin surface and generating an electric signal representative of said electrical activity; a voltage averaging means connected to said sensing means to average the voltage potential sensed by said sensing means; analog to digital converter means connected to said sensing means to convert analog signals from said sensing means into digital signals; a microprocessor means connected to said averaging means and to said converter means to record and microprocess electric signals from said averaging means and said sensing means; an alarm connected to said microprocessor means adapted to be triggered by said microprocessor means according to preselected criteria; a display means connected to said microprocessor means to display electrical signals representative of cardiac activity being sensed; a battery powering said electrical activity sensing means, said voltage averaging means, said analog to digital converter means, said microprocessor means, said alarm, and said display means; a durable, light-weight housing within which said device is hermetically sealed.

4. Device of claim 3 wherein: a first and a second electrode means and one common ground electrode of said cardiac electrical activity sensing means are adapted to be placed on the upper wrist-lower forearm with each of said sensing electrodes placed at different distances form the heart; means provided for subtracting electrical potential sensed by said first electrode means and by said second electrode means, which difference is the potential which is amplified and fed to said voltage averager means and said microprocessor means.

5. Device comprising: a semi-permeable membrane adapted for islet beta cells to be positioned proximate to one side of said semi-permeable membrane; means for sensing electrical activity representative of insulin-secreting activity of said beta cells; housing means to seal-in beta cells and electrode assembly means adapted to be proximate said beta cells, said electrode assembly means being a part of said sensing means; an analog to digital converter connected to said sensing means to convert an analog signal from said sensing means into a digital signal; a microprocessor means connected to said converter to receive said digital signal; and a display means connected to said microprocessor means to receive and display a read-out representative of said insulin secreting activity of said beta cells.

* * * * *